United States Patent [19]
Hironaga et al.

[11] Patent Number: 6,064,473
[45] Date of Patent: May 16, 2000

[54] PARTICLE MEASURING APPARATUS AND ITS CALIBRATION METHOD

[75] Inventors: Katsuji Hironaga, Kawanishi; Akira Tsunemi, Suita; Koji Ueyama, Osaka, all of Japan

[73] Assignee: Kanomax Japan Incorporated, Suita, Japan

[21] Appl. No.: 09/060,336

[22] Filed: Apr. 15, 1998

[30] Foreign Application Priority Data

Apr. 15, 1997 [JP] Japan ................................. 9-097492

[51] Int. Cl.⁷ ............................... G01P 3/36; G01B 11/02
[52] U.S. Cl. .......................................... 356/28.5; 356/355
[58] Field of Search .................... 356/28.5, 355

[56] References Cited

U.S. PATENT DOCUMENTS

| | | |
|---|---|---|
| 3,830,568 | 8/1974 | Allen . |
| 4,537,507 | 8/1985 | Hess ........................ 356/28.5 |
| 4,859,055 | 8/1989 | Gal et al. . |
| 4,997,272 | 3/1991 | Dopheide et al. ............ 356/28.5 |

FOREIGN PATENT DOCUMENTS

| | | | |
|---|---|---|---|
| 4128966 | 3/1993 | Germany ................ | 356/28.5 |
| 7-55693 | 3/1995 | Japan . | |

*Primary Examiner*—Stephen C. Buczinski
*Attorney, Agent, or Firm*—McDermott, Will & Emery

[57] ABSTRACT

In a particle measuring apparatus using laser Doppler velocimeter, it is intended to facilitate calibration of the apparatus for measuring the shape of particle. Laser beams passing through a first intersecting region M1 which is a measuring region are intersected again by using condenser lenses 21 and 22, and a second intersecting region M2 is formed. The intersecting region M2 is magnified by a magnifying lens 23. An optical bundle fiber 24 is brought closer from afar to the lens 23, and set at a position where AC component is not formed. As a result, the size of the incident portion of each optical fiber 24$i$ and the fringe interval $d_f$ may be matched equivalently, so that the absolute value of the shape of particle may be obtained.

12 Claims, 11 Drawing Sheets

FIG. 4(a) 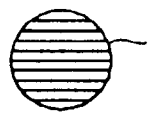 M1 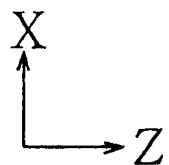
  M2

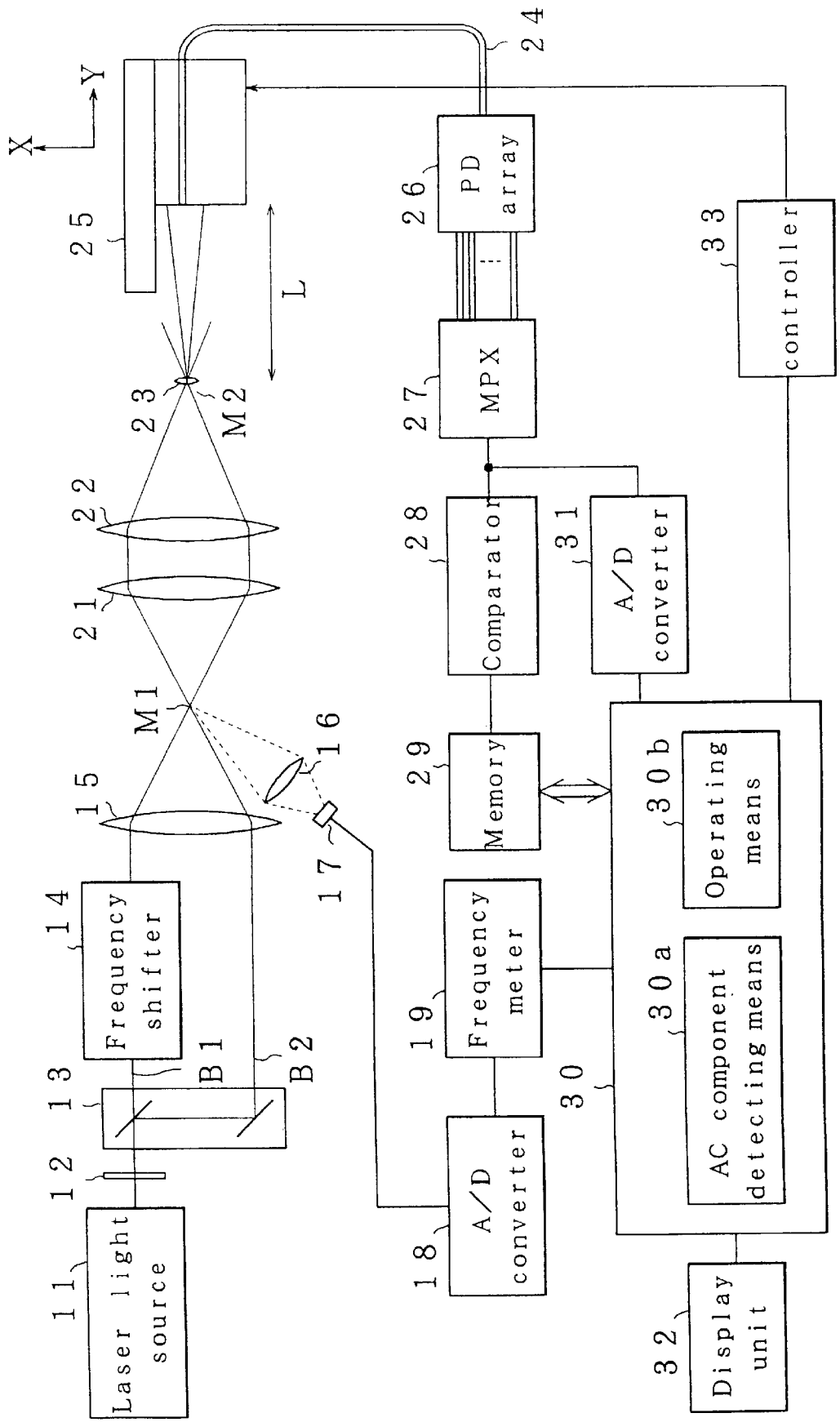

PARTICLE MEASURING APPARATUS AND ITS CALIBRATION METHOD

FIELD OF THE INVENTION

The present invention relates to a particle measuring apparatus for measuring the velocity and/or shape of particles, by detecting shadows of particles passing through a measuring region in air or in liquid, by using a laser Doppler velocimeter, and its calibration method.

PRIOR ART

As an apparatus for measuring the velocity of fine particles floating in the air, a laser Doppler velocimeter is used. In the laser Doppler velocimeter, two laser beams are crossed, and a set of interference fringes is formed at the intersecting region, and the velocity of a particle passing through the intersecting region is detected on the basis of the frequency of the scattering light. In such laser Doppler velocimeter, the velocity of particles can be measured, but the shape information of particles could not be obtained.

Japanese Laid-open Patent No. 7-55693 proposes a particle measuring apparatus, using this laser Doppler velocimeter, for further magnifying the intersecting region by using an optical system to form a second intersecting region, disposing an one-dimensional photoelectric conversion element at a position in the second intersecting region, and measuring the shape of a particle on the basis of the shadow of the particle crossing the intersecting region.

FIG. 10 is a block diagram showing an example of such particle measuring apparatus. In the particle measuring apparatus, as shown in the drawing, a beam splitter 101 is disposed ahead of a laser light source 100, a laser beam is separated into two lines of laser light, their frequency is shifted by frequency shifters 102 and 103, and they are intersected at one point by a condenser lens 104. By intersecting, a set of interference fringes is formed in the intersecting region. A photoelectric conversion element 105 and a frequency meter 106 are to measure the passing velocity of a particle on the basis of the frequency of the scattering light of the particle passing through the intersecting region. The laser beams forming this intersecting region are focused again by using lenses 107 and 108. A line sensor 109, photo detectiny elements in a row is disposed at a position converged by the lens 108, and a photoelectric conversion signal obtained from the line sensor 109 at a specific velocity is taken into an operating means 112 through a multiplexer (MFX) 110 and an A/D converter 111. Thus, the shape of the particle can be measured by the operating means 112 by the velocity of the particle passing through the intersecting region and the information from the line sensor 109.

In such conventional particle measuring apparatus, to measure the shape of the particle passing through the measuring region accurately, it is necessary to calibrate the apparatus precisely. In the conventional particle measuring apparatus, such calibration was difficult, and it was necessary to calibrate the measuring apparatus by actually passing a spherical particle of a known particle size.

SUMMARY OF THE INVENTION

The present invention is devised to solve the problems of the conventional particle measuring apparatus, and it is hence an object thereof to present a particle measuring apparatus easy to calibrate for measuring the particle size and capable of measuring accurately, and its calibration method.

According to the invention, only by bringing the incident position of a photoelectric converting means closer toward a magnifying lens, the size of each element of the photoelectric converting element can be very easily adjusted to coincide equivalently with a fringe distance in an intersecting region. Hence, the calibration work when using the particle measuring apparatus can be extremely simplified, and it is very easy to use.

BRIEF DESCRIPTION OF THE DRAWINGS

FIG. 11 is a block diagram showing a particle measuring apparatus and calibration mechanism in a second embodiment of the invention.

DESCRIPTION OF THE PREFERRED EMBODIMENT

Figure 1:
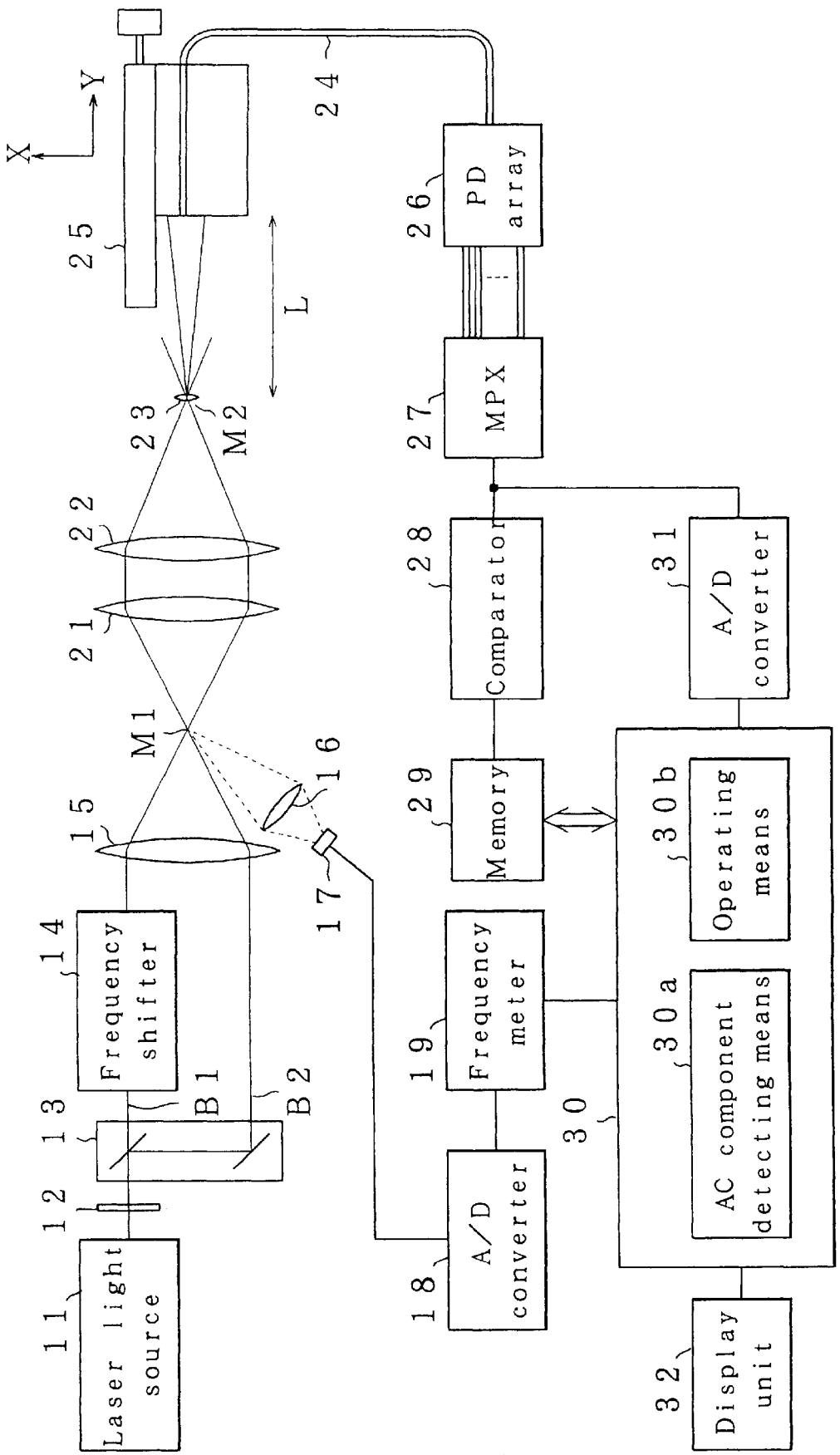
FIG. 1 is a block diagram showing a particle measuring apparatus and calibration mechanism in a first embodiment of the invention.
Figure 2:
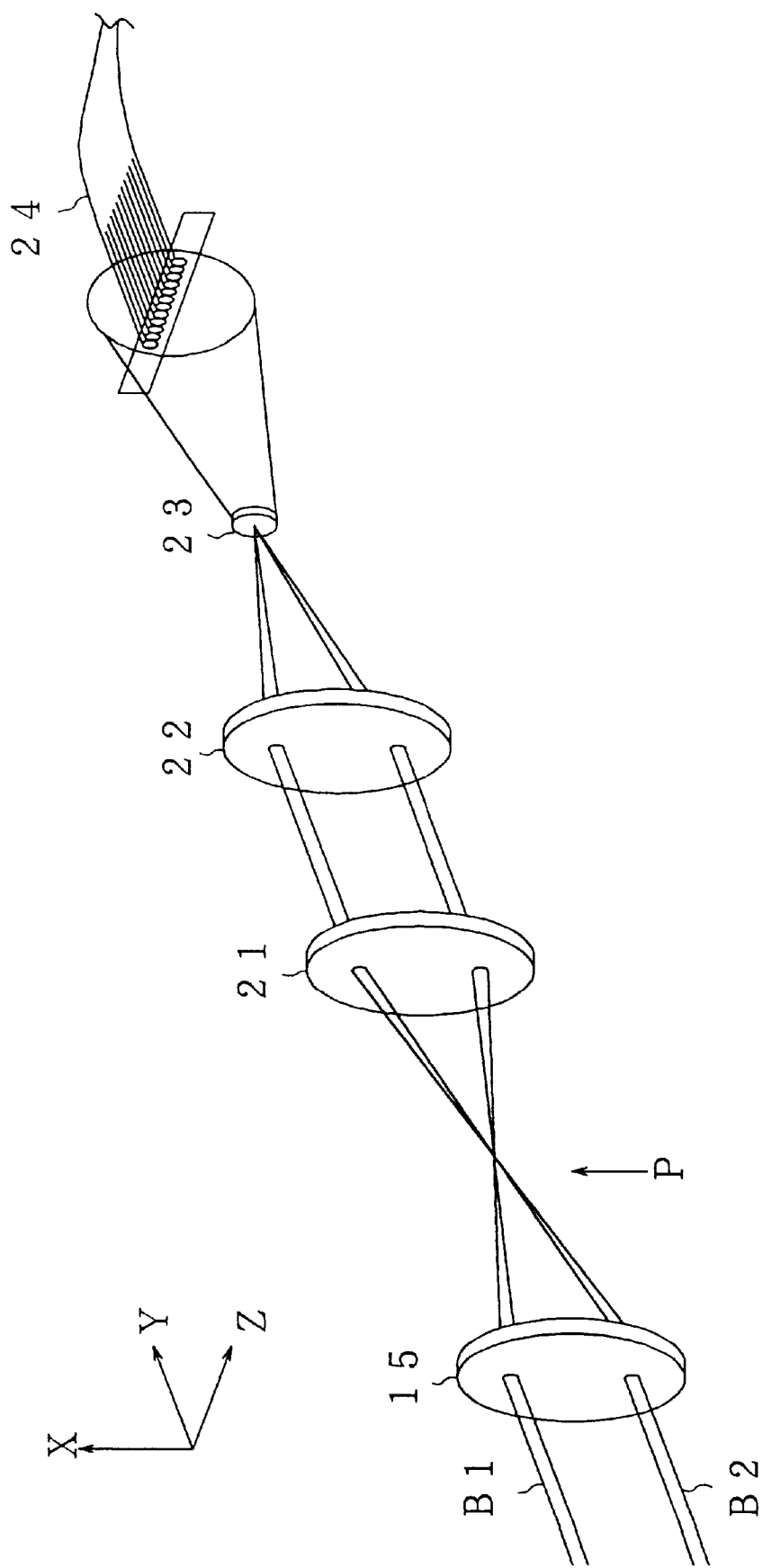
FIG. 2 is a perspective view showing a constitution of optical system of the particle measuring apparatus in the embodiment.

FIG. 1 is a block diagram showing principal parts of a particle measuring apparatus in the first embodiment of the invention, and its calibration method, and FIG. 2 is a perspective view showing parts of its optical system. As shown in the drawings, a laser beam is generated by a laser light source 11, and is emitted to a polarizer 12. If the laser light source 11 generates linearly polarized laser light, the polarizer 12 is not necessary. The linearly polarized laser light beam is incident to a beam splitter 13 through the polarizer 12. The beam splitter 13 splits the laser beam into two parallel laser beams B1, B2 of the same intensity, and one laser beam is provided with a frequency shifter 14, for example, a Bragg cell for shifting the frequency. A condenser lens 15 is designed to focus two parallel laser beams at one point. The laser light source 11, the polarizer 12, the beam splitter 13, the frequency shifter 14, and the condenser lens 15 compose a light source means for forming a first set of interference fringes by focusing and intersecting two laser beams having a specific frequency difference. In this constitution, same as the conventional particle measuring apparatus, a collecting lens 16 is disposed for detecting the scattering light from a first intersecting region, and a photo diode 17 is disposed at its focus position. The photo diode 17 is a photoelectric converter for detecting the scattering light. Its output is given to a frequency meter 19 through an A/D converter 18. The frequency meter 19 measures the frequency of intensity change of the scattering light of the particle passing through the fringes so as to obtain the velocity information of the particle.

On the other hand, lenses 21 and 22 are a condensing means for focusing the light passing through the first intersecting region again at one point. The lenses 21 and 22 have focal lengths f1 and f2, respectively and the focal length f1 of the lens 21 is matched with the interval from the lens 21 to the first intersecting region. In this manner, the laser beam is converted again into parallel beams by the lens 21. Moreover, the lens 22 is intended to intersect the parallel laser beams again. Thus, a second set of interference fringes at a second intersecting region is formed at the focusing position of the two laser beams by the lens 22.

Further, in the invention, the second set of interference fringes of the second intersecting region is magnified by a magnifying lens 23. The magnifying lens 23 is a lens of an extremely short focal length, and is designed to magnify the light forming the second intersecting region directly as diffusion light. The magnifying lens 23 is located nearly in the second intersecting region, and a screen is disposed at a side to define its position accurately, and the magnifying lens 23 is positioned so as to focus at the screen position. As a result, the magnified fringe can be received in a specific range. To receive thus diffused light, an optical bundle fiber 24 is provided as shown in FIG. 1 and FIG. 2. In this embodiment, the optical bundle fiber 24 is provided in a plurality, for example, 64 optical fibers 24a to 24n are matched at one end, and linearly arranged in a row along the Z-axis. The end face of the optical bundle fiber 24 confronts the magnifying lens 23, and is fixed on a moving mechanism 25. The moving mechanism 25 is a position adjuster for adjusting the position by moving the optical bundle fiber 24 in the direction of Y-axis in the drawing.

At the other end of the optical bundle fiber 24, a photoelectric conversion element, for example, photo diode array (PD array) 26 is disposed to detect the light reception level of each fiber. The photo diode array 26 is to convert the light emitted from each optical fiber photoelectrically, and it composes the photoelectric converter together with the optical bundle fiber 24. The photoelectric conversion output of the photo diode array 26 is amplified, and put into a multiplexer (MPX) 27. The multiplexer 27 multiplexes the photoelectric conversion output in a specific period, and its output is given to a comparator 28. The comparator 28 discriminates the input signal from the multiplexer 27 by three values, that is, a shadow state by shielding both laser beams B1 and B2, a half-shadow state by shielding either one of the laser beams B1 and B2, and a shadow-less state by receiving both laser beams, and its output is given to a memory 29. Any output from the multiplexer 27 is put into an operation unit 30 through an A/D converter 31. The memory 29 stores the particle image according to the photoelectric conversion signal from each fiber when a detection signal of Doppler frequency is obtained after the optical bundle fiber 24 is set in a specified position. The operation unit 30 is composed of a microprocessor, and has a function of an AC component detecting means 30a for detecting the level of AC signal and displaying in a display unit 32, in order to adjust the position of the optical fiber so that the AC component of the signal from the A/D converter 31 may be zero as mentioned below. The operation unit 30 also receives the output of the frequency meter 19 mentioned above, and has a function of an operating means 30b for composing the shape of the particle passing through the first intersecting region on the basis of the data of the image held once in the memory 29.

Figure 3A:
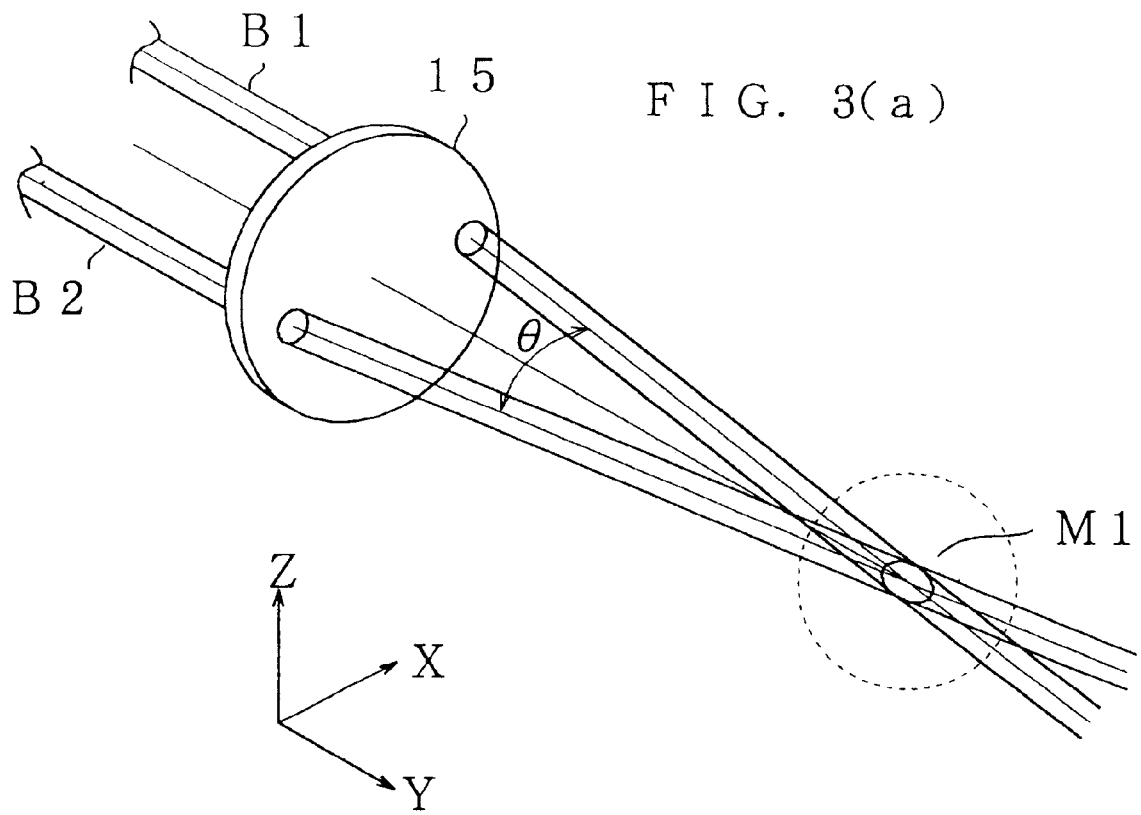
FIG. 3 ($a$) is a perspective view showing a condenser lens and a first intersecting region of the particle measuring apparatus in the embodiment, and ($b$) is its magnified view.
Figure 3B:
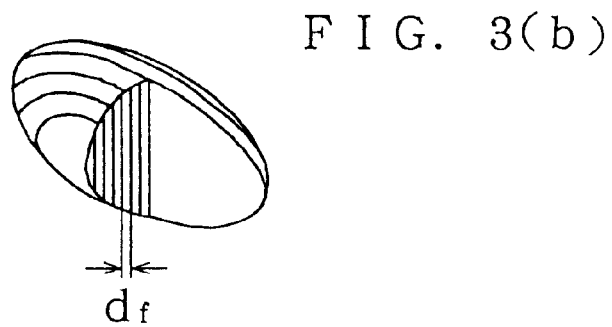

In this embodiment, the operation is described below. Laser light is emitted from the laser light source 11, and the light is separated by the beam splitter 13 through the polarizer 12 into two laser beams B1 and B2 of same intensity. The laser beam B1 is fed into the frequency shifter 14 and is shifted in frequency. The shifting frequency $f_s$ is varied depending on the particle velocity, and is, for example, several MHz to scores of MHz. The beams are crossed at a measuring region by the condenser lens 15. FIG. 3 is a diagram showing this lens 15, laser beams B1, B2, and the first intersecting region M1. The intersection region M1 is a region shaped like an elliptical rotating element formed by two intersecting laser beams, and the set of interference fringes is formed as shown in the diagram. The fringe interval $d_f$ is expressed as follows, assuming the intersecting angle of the laser beams B1 and B2 to be θ, and the wavelength of the laser beam to be λ.

$$d_f = \lambda / \{2 \sin(\theta/2)\}$$

Without using the frequency shifter 14, the fringes are fixed, but when the frequency of one laser beam is shifted by using the frequency shifter 14, the fringes are also moved along with the shift frequency $f_s$. At this time, the fringe interval $d_f$ formed in the intersecting region M1 is constant. Therefore, when a fine particle passes in the direction of the X-axis in the drawing, if the fine particle passes through this intersecting region M1, the intensity of the scattering light varies depending on the fringes. Therefore, detecting the scattering light by the collecting lens 16 and the photoelectric converter 17, and measuring its frequency $f_p$ using the frequency meter 19, the velocity of the particle can be calculated in the following formula. It is also possible to measure the direction of the particle by the direction of change of frequency. That is, the Doppler frequency $f_d$ is calculated in the following formula.

$$f_d = f_s - f_p$$

By measuring the Doppler frequency $f_d$, the velocity V of the particle is expressed in the following formula.

$$V = d_f \times f_d$$

Figure 4B:
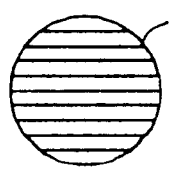
FIGS. 4($a$)–4($c$) are diagrams showing first and second sets of interference fringes at first and second intersecting regions, a magnified third intersecting region, and an optical bundle fiber of the particle measuring apparatus in the embodiment.
Figure 4C:
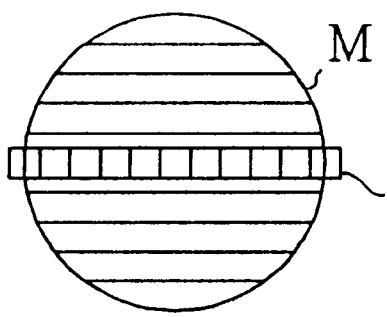

Consequently, as shown in FIGS. 4 (a), and (b), the laser beams B1 and B2 forming the first intersecting region M1 are focused again by the lenses 21, 22, and a second intersecting region M2 is formed. The first intersecting region M1 is, as compared with the second intersecting region M2, magnified by the focus ratio of the lenses 21 and 22, and the magnification rate X1 is expressed as follows.

$$X1 = f2/f1$$

Figure 5A:
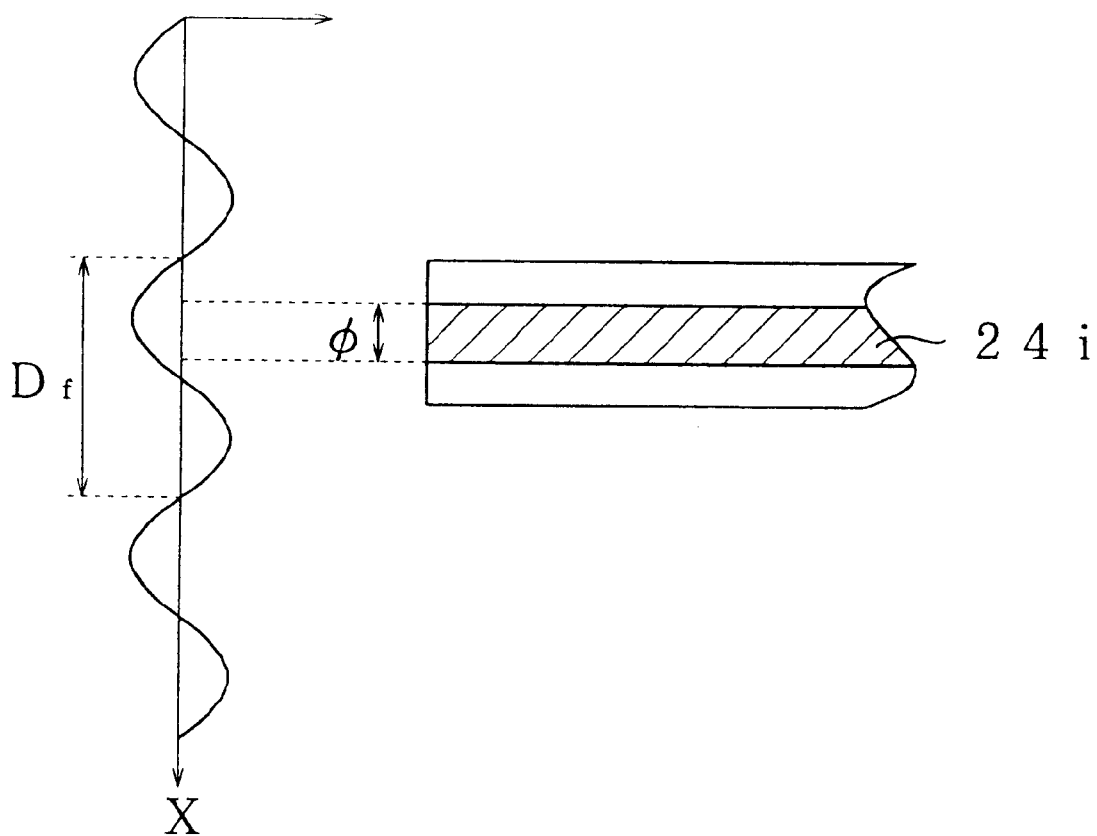
FIGS. 5($a$)–5($b$) are diagrams showing the optical bundle fiber, the magnified fringes received in an optical fiber, and its photoelectric conversion signal in the embodiment (1).
Figure 5B:
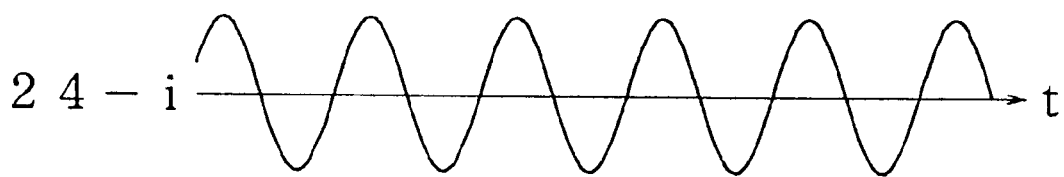
Figure 6A:
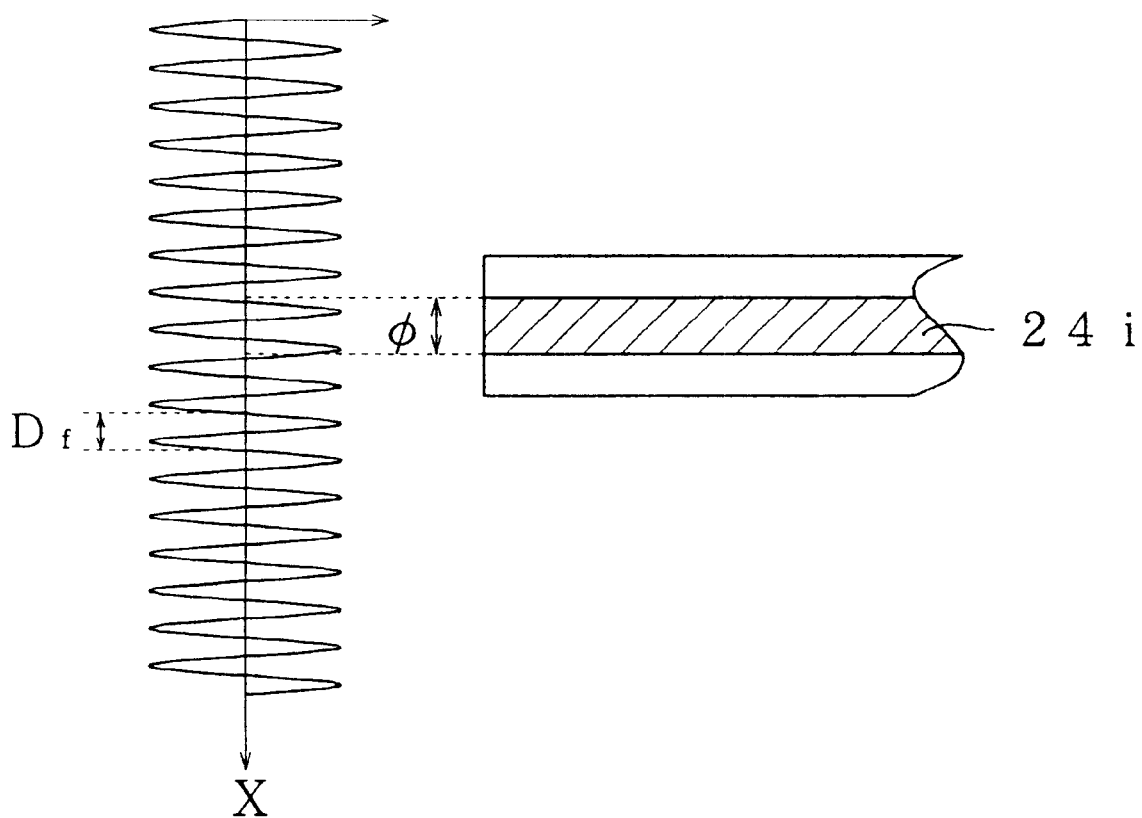
FIGS. 6($a$)–6($b$) are diagrams showing the optical fiber, the magnified fringes received in the optical fiber, and its photoelectric conversion signal in the embodiment (2).
Figure 6B:
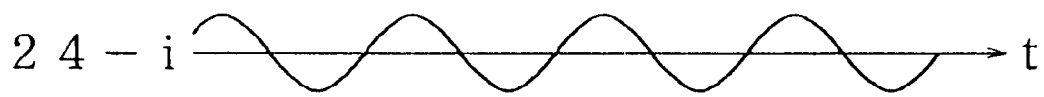
Figure 7A:
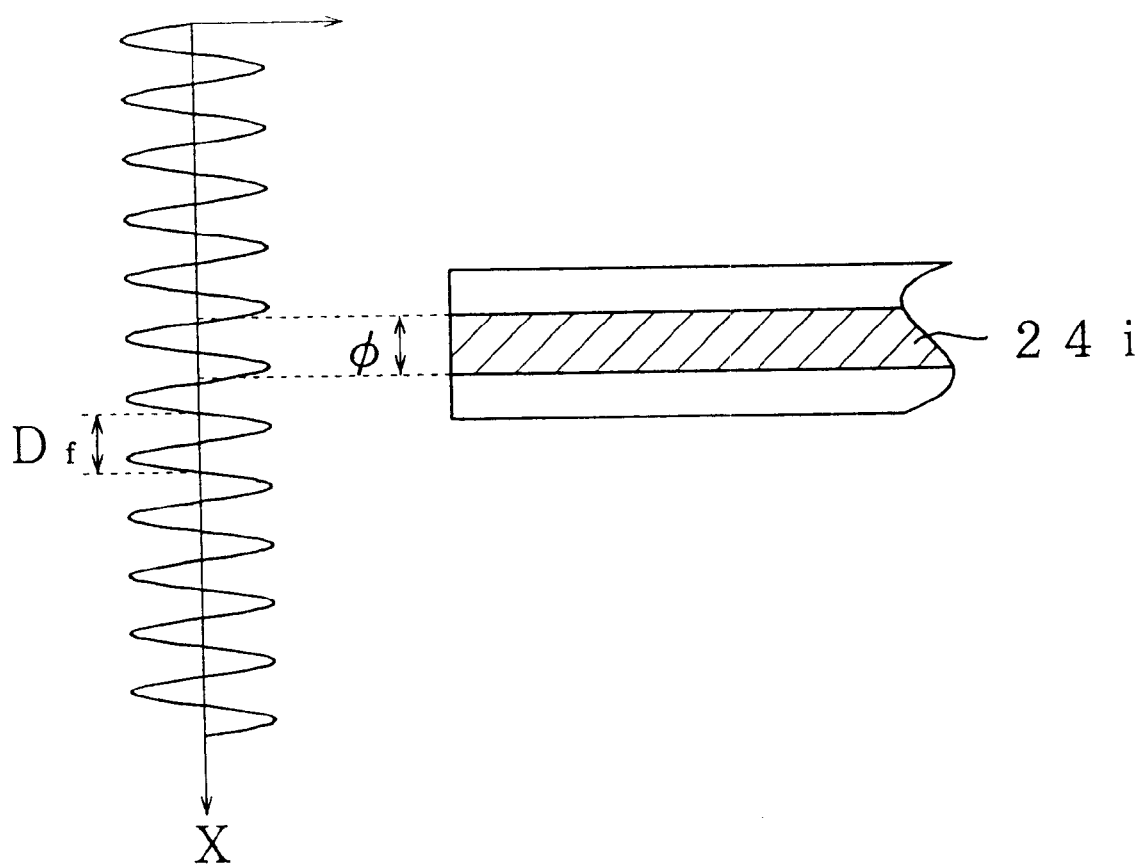
FIGS. 7($a$)–7($b$) are diagrams showing the optical fiber, the magnified fringes received in the optical fiber, and its photoelectric conversion signal in the embodiment (3).
Figure 7B:
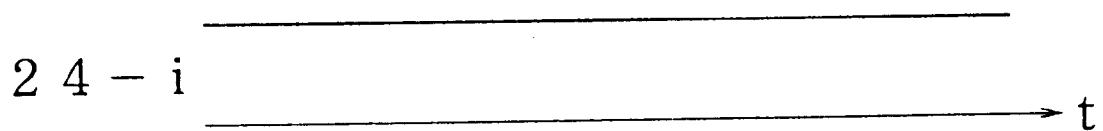

The second intersecting region M2 is magnified by the magnifying lens 23. FIG. 4 (c) shows the optical bundle fiber 24 and the shape of the magnified second intersecting region M2 at the end of the optical bundle fiber 24. The magnification rate X2 from the second intersecting region M2 to the end of the optical bundle fiber 24 corresponds to the distance from the magnifying lens 23 to the end of the optical bundle fiber 24, but it is not easy to measure the magnification rate X2. In the invention, therefore, the distance between the end of the optical bundle fiber 24 and the magnifying lens 23 is varied by the moving mechanism 25. FIG. 5 to FIG. 7 show the optical bundle fiber 24 at different distances L, the fringe in the magnified intersecting region M3 getting into each optical fiber, and the photoelectric conversion signal from one optical fiber 24$i$. Supposing the core diameter of incidence of light of each optical fiber 24$i$ to be $\phi$, the photoelectric conversion signal obtained in each fiber corresponds to the brightness of the magnified fringes. When this brightness is expressed by a sine curve as shown in FIG. 5 ($a$) to FIG. 7 ($a$), the photoelectric conversion signal is also the level corresponding to the brightness. As mentioned above, since the laser beam B1 is changed from the original laser light by the shift frequency $f_s$, the fringe pattern itself is moved at a velocity corresponding to the shift frequency $f_s$. Therefore, the photoelectric conversion output obtained in each optical fiber is also changed in time. FIG. 5 ($b$) to FIG. 7 ($b$) are waveform diagrams showing such time changes, and the frequency coincides with the shift frequency $f_s$. However, if it is impossible to measure due to high frequency of $f_s$, the laser beam B2 may be also provided with a frequency shifter at a different frequency from $f_s$, so that the shift frequency may be the difference of both shift frequencies, and hence the frequency can be lowered.

When the end face of the optical bundle fiber 24 is set away from the lens 23, the magnification rate of the third intersecting region M3 becomes large as shown in FIG. 5, and the interval $D_f$ of the magnified fringe is larger than $\phi$ ($\phi < D_f$). Therefore, as shown in FIG. 5 ($b$), a sine wave is obtained from each fiber. When the end face of the optical bundle fiber 24 is brought closer to the magnifying lens 23, as shown in FIG. 6, the interval $D_f$ of the magnified fringes becomes relatively smaller ($\phi > D_f$). Therefore, when the end face of the optical bundle fiber 24 is adjusted to be closer to the lens 23 gradually from afar, the core diameter $\phi$ of the optical fiber 24$i$ reaches the position coinciding with the interval $D_f$ of the magnified fringes. At this position $\phi = D_f$, as shown in FIG. 7 ($a$), the fringes move along the time axis, but regardless of the move of the fringes, a photoelectric conversion signal from optical fiber 24$i$ keeps a constant level. That is, the photoelectric conversion output of the optical fiber is a DC component. Such change occurs simultaneously in all optical fibers.

Figure 8:
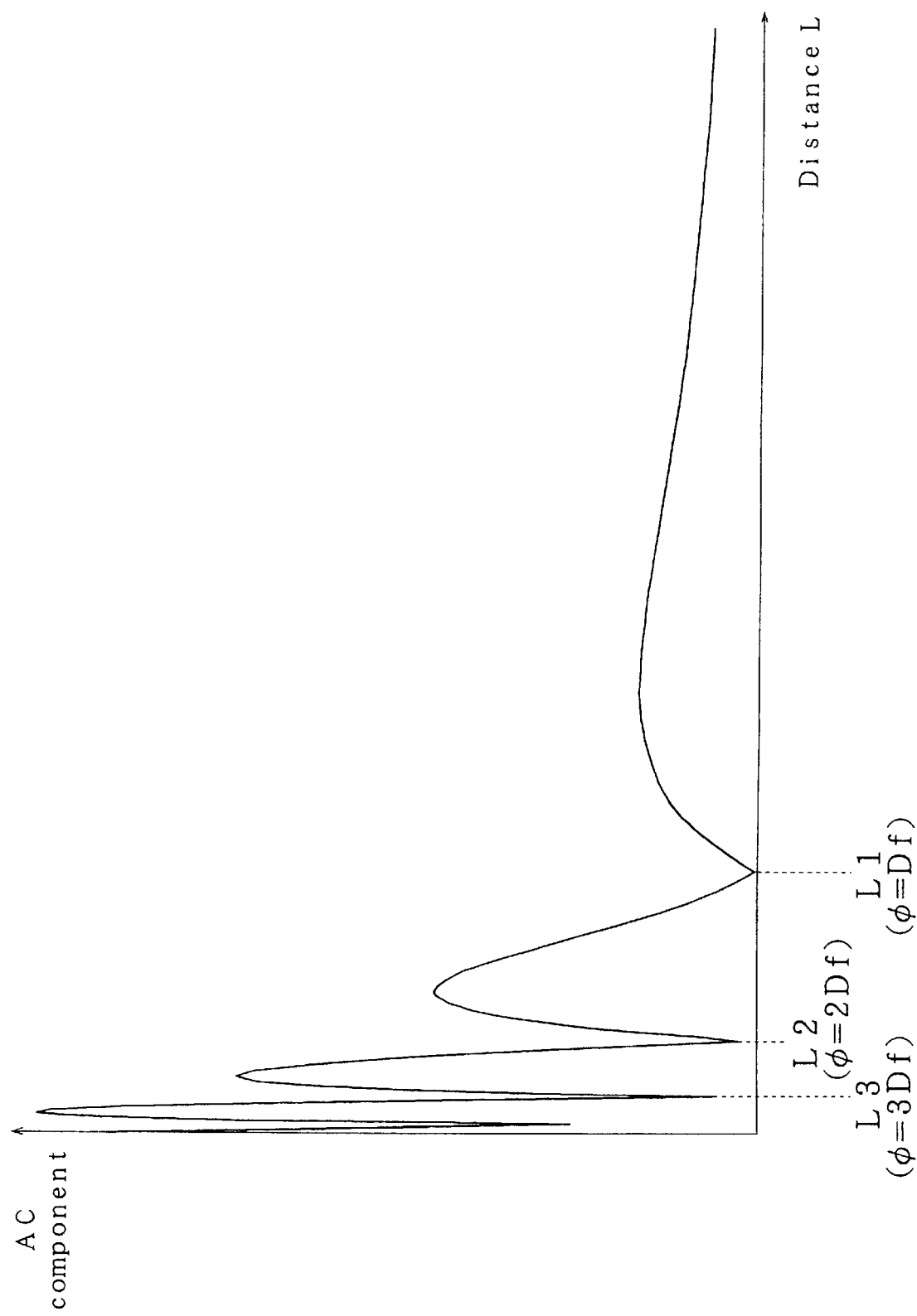
FIG. 8 is a graph showing changes of amplitude of AC signal received in the optical fiber at an interval L from the second intersecting region to the optical bundle fiber.

FIG. 8 is a diagram showing changes of amplitude of AC component of photoelectric conversion signal corresponding to the distance L from the end face of optical fiber to the magnifying lens 23 in one optical fiber 24$i$. When the optical bundle fiber 24 is brought closer to the lens 23 from afar as shown in the diagram by the moving mechanism 25, it first reaches the distance L1 where the AC component is nearly zero level. This distance L1 shows the point of coincidence of the core diameter $\phi$ of the optical fiber with the interval $D_f$, and the amplitude of each optical fiber is the same. Further, at distance L2, again, the AC component of the photoelectric conversion value of the optical fiber is nearly zero. This position is a second zero level point where $2D_f$ coincides with $\phi$. Similarly, the photoelectric conversion value is nearly zero at the point of $3D_f = \phi$. In this embodiment, it is adjusted by the moving mechanism 25 so that the optical fiber may be positioned at distance L1 where $D_f$ coincides with $\phi$. This can be adjusted by bringing the optical bundle fiber 24 closer to the magnifying lens 23 from afar, checking the level of the AC component calculated by the operating means 30 by the display unit 32, and setting in the first position where the AC component is nearly zero.

Figure 9A:
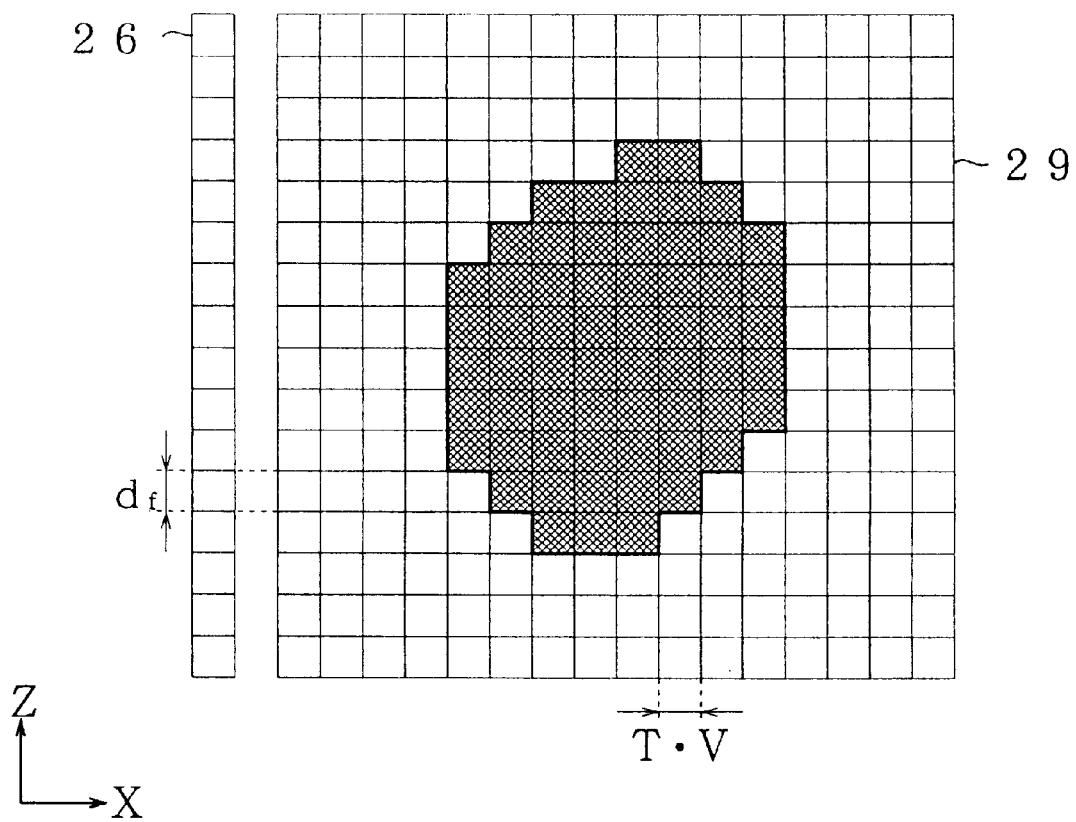
FIGS. 9($a$)–9($b$) are diagrams showing image information reconstructed in a memory 29.
Figure 9B:
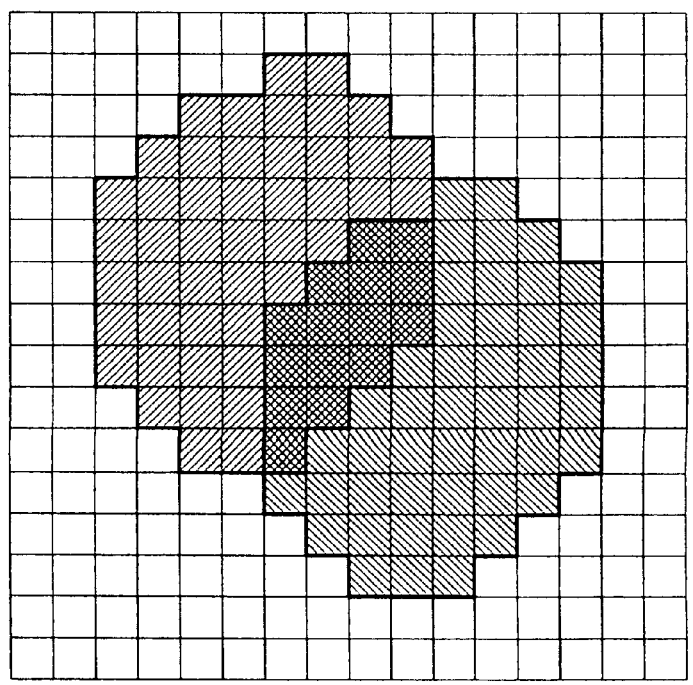
Figure 10:
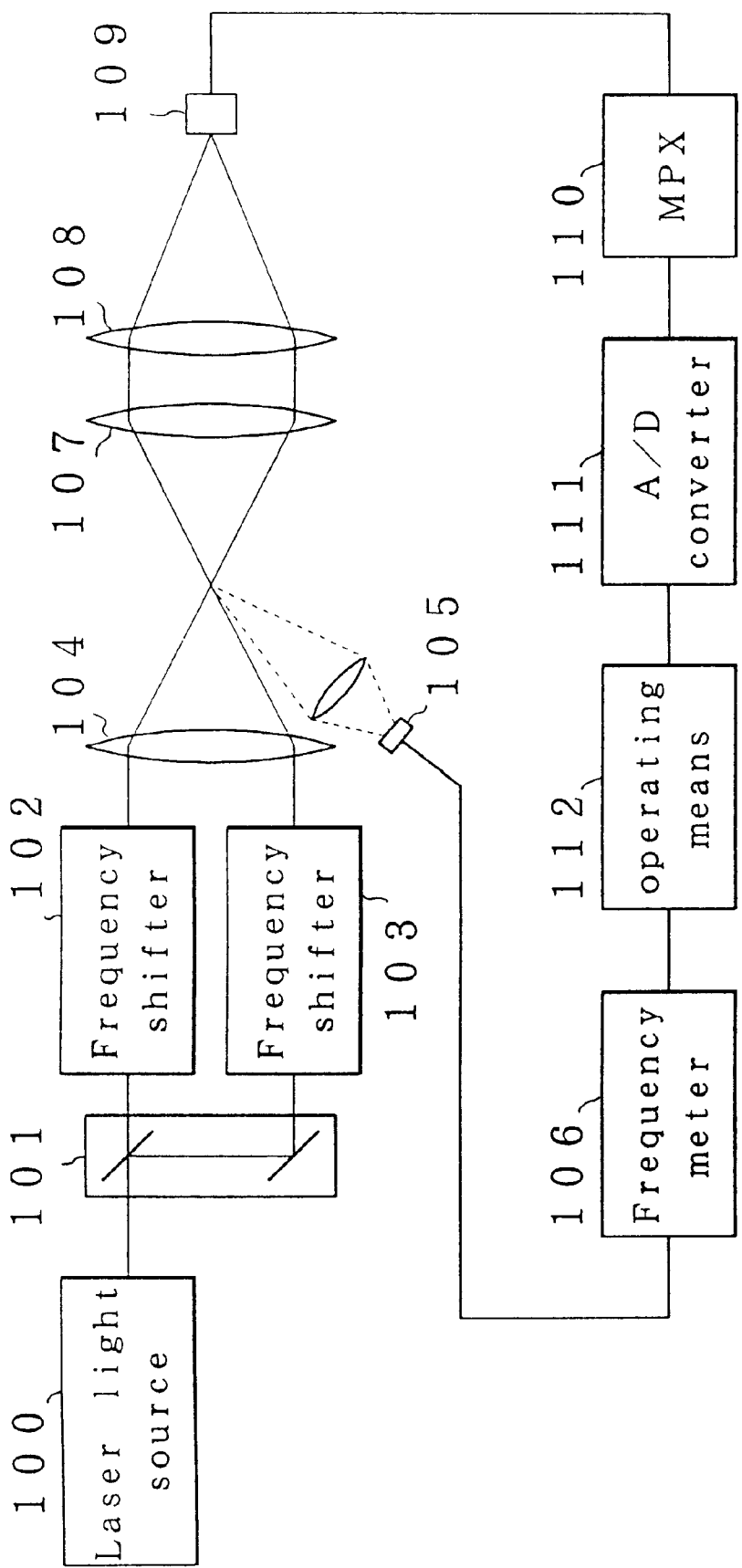
FIG. 10 is a block diagram showing a conventional particle measuring apparatus.

When the adjustment is over in this manner, the size of each pixel coincides with the interval of the fringes. That is, the resolution of the particle shape of the particle passing the first intersecting region M1 as the measuring point coincides with the interval $d_f$ of the fringes. That is, same as in the laser Doppler velocimeter, it is possible to detect the shape of the particle without calibrating by actual particle. In this state of adjustment of position in this manner, when the particle p passing the center of the first intersecting region M1 in the X-axis direction is measured, the velocity V of the particle is obtained by the frequency meter 19. At this time, the time resolution of the photoelectric conversion value held in the memory 29 corresponds to the velocity component. FIG. 9 ($a$) shows an image reconstructed along the time axis from the output obtained in the photo diode array 26. It is thus possible to reconstruct the image to which the shadow of the particle is projected, from the output of the linear photo diode array 26 obtained in the time series, and the shape of the particle passing through the intersecting region can be measured. In this image, the resolution of one pixel in the Z-axis direction vertical to the sheet of paper in FIG. 1 is the interval $d_f$ of the fringe. Incidentally, one pixel in the X-axis direction in FIG. 1 is determined by the product T·V of the interval T of the time of one line being readout from the photo diode array and the particle velocity V. Thus, the size of the particle can be recognized, and the shape of the particle can be measured. In FIG. 9, the number of the optical fibers is 16.

Usually, the particle does not pass the center of the first intersecting region M1 but is deviated in position, and in this case since either laser beam is shielded, the image held in the memory 29 is as shown in FIG. 9 ($b$). Therefore, by the process for eliminating one of the overlapping shadows, the image of the shadow can be reconstructed. From the two shadow images, the moving direction of the particle can be measured simultaneously as the vector.

In the foregoing embodiment, the optical bundle fiber is moved by the moving mechanism 25, and the other end is photoelectrically converted by the photoelectric converting element, but it is also possible to arrange one-dimensional photoelectric converting elements directly at the position of the end face of the optical bundle fiber.

In the first embodiment, the end face of the optical bundle fiber 24 is gradually brought closer to the magnifying lens 23 by the moving mechanism 25 so that the AC component displayed in the display unit 32 becomes zero, but by moving the optical bundle fiber 24 automatically by the moving mechanism 25, it is also possible to compose to stop at the position where the AC component becomes zero.

In the second embodiment of the present invention, as shown in FIG. 11, the position adjuster comprises the moving mechanism 25 and a controller 33. The controller 33 receives the AC component of the AC component detecting means 30$a$ and controls the position of the end face of the optical bandle filter 24 where the Ac component becomes zero.

We claim:

1. A particle measuring apparatus comprising:
   a light source means for forming a first set of interference fringes in a first intersecting region by focusing and intersecting two laser beams having a specific frequency difference;
   a particle velocity measuring means for measuring the velocity of a particle passing through said first intersecting region on the basis of the frequency of scattering light;
   a condensing means for forming a second set of interference fringes in a second intersecting region by intersecting again the laser beams forming said first intersecting region;

a magnifying means for magnifying optically said second set of interference fringes forming in said second intersecting region;

a photoelectric converter including plural photoelectric converting elements linearly arranging incident end faces so as to confront said magnifying means;

an AC component detector which detects an AC component of the photoelectric conversion signal having the frequency of said specific frequency difference of said light source means obtained from any photoelectric converting element of said photoelectric converter;

a position adjuster which adjusts the position of said photoelectric converter at a position where the AC component detected by said AC component detector becomes zero; and an operating means for composing the shape of the particle, by the particle velocity signal from said particle velocity measuring means, and the time series projection shape of the particle from said plural photoelectric converting elements of said photoelectric converter.

2. A particle measuring apparatus according to claim 1, wherein said light source means comprises:

a laser light source which generates a linearly polarized laser light beam;

a beam splitter which splits said laser light beam of said laser light source into two laser beams;

a frequency shifter which shifts the frequency of one of said splitted laser beams; and a condenser lens for focussing two laser beams at one point.

3. A particle measuring apparatus according to claim 1, wherein said light source means comprises:

a laser light source which generates a laser light beam;

a polarizer in which a laser light beam of said laser light source is passing;

a beam splitter which splits said laser light beam through said polarizer into two laser beams;

a frequency shifter which shifts the frequency of one of said splitted laser beams; and a condenser lens for focussing two laser beams at one point.

4. A particle measuring apparatus according to claim 1, wherein said magnifying means is a magnifying lens.

5. A particle measuring apparatus according to claim 1, wherein said photoelectric converting means comprises:

an optical bundle fiber by plural of optical fibers arranged in a row in a direction vertical to the plane forming two laser beams so that the incident end faces confront said magnifying means; and plural photoelectric converting elements arranged respectively at end faces of said optical fibers, for converting the light from each optical fiber into electric signals.

6. A particle measuring apparatus according to claim 1, wherein said photoelectric converting means comprises:

plural photoelectric converting elements arranged in a row in a direction vertical to the plane forming two laser beams so that the incident faces thereof confront said magnifying means, for converting the light of said plane into electric signals.

7. A particle measuring apparatus according to claim 1, said particle measuring apparatus further comprises:

a display unit for displaying the AC component level of said AC component detecter.

8. A particle measuring apparatus according to claim 1, wherein said position adjuster is a moving mechanism which adjusts the distance between said magnifying means and said the incident position of said photoelectric converter.

9. A particle measuring apparatus according to claim 1, wherein said position adjuster comprises:

a moving mechanism which adjusts the distance between said magnifying means and said the incident position of said photoelectric converer; and a controller which controls the position of the incident position of the photoelectric converter where the AC component by said AC component detecter becomes zero.

10. A particle measuring apparatus according to claim 1, wherein said position adjuster brings the incident position of said photoelectric converter closer to said magnifying means from afar, and setting at a position where the AC component by said AC component detecter first becomes zero.

11. A calibration method of said particle measuring apparatus according to claim 1, characterized by the following steps of magnifying said second set of interference fringes formed in said second intersecting region by a magnifying lens;

comfronting said photoelectric converter to said magnifying means; and adjusting the distance between said magnifying means and said incident position of said photoelectric converter in a manner that the AC component of the photoelectric conversion signal obtained from any one of the photoelectric converting elements becomes zero.

12. A calibration method of said particle measuring apparatus according to claim 11, wherein said position adjusing is achieved by bringing the photoelectric converter closer to the magnifying means from afar, and setting at a position where the AC component first becomes zero.

* * * * *